United States Patent [19]

Mabilat et al.

[11] Patent Number: 5,589,585
[45] Date of Patent: Dec. 31, 1996

[54] DNA FRAGMENTS, PROBES AND AMPLIFICATION PRIMERS OF THE 65 KD ANTIGEN OF MYCOBACTERIA

[75] Inventors: Claude Mabilat, Villeurbanne, France; Jean-Claude Pechere, Geneva, Switzerland

[73] Assignee: Bio Merieux, L'Etoile, France

[21] Appl. No.: 105,168

[22] Filed: Aug. 12, 1993

[30] Foreign Application Priority Data

Aug. 12, 1992 [FR] France ................................. 92 10094

[51] Int. Cl.$^6$ .................................................. C07H 21/04
[52] U.S. Cl. ................... 536/24.32; 536/23.7; 536/24.33
[58] Field of Search ...................... 435/6, 91.2; 536/23.7, 536/24.32, 24.33

[56] References Cited

FOREIGN PATENT DOCUMENTS

| | | |
|---|---|---|
| WO88/00974 | 2/1988 | WIPO . |
| WO88/05823 | 8/1988 | WIPO . |
| WO88/06591 | 9/1988 | WIPO . |
| WO90/12875 | 11/1990 | WIPO . |
| WO91/19812 | 12/1991 | WIPO . |

OTHER PUBLICATIONS

Wayne et al., "Family Mycobacteriaceae Chester 1897, 63$^{AL*}$, " Section 16, Mycobacteria, *Bergey's Manual of Systemic Bacteriology*, vol. 2, 1986, pp. 1436–1457.

Styblo, K. MD., "The Kellersberger Memorial Lecture, 1982$^1$, Tuberculosis and its Control: Lessons to be Learned From Past Experience, and Implications for Leprosy Control Programmes," *Ethiop. Med. J.*, 21, pp. 101–122.

Engers, H. D., et al., "Results of a World Health Organization–Sponsored Workshop to Characterize Antigens Recognized by Mycobacterium–Specific Monoclonal Antibodies," *Infection and Immunity*, vol. 51, 1986, pp. 718–720.

Kiehn, Timothy E., et al., "Infections Caused by Mycobacterium avium Complex in Immunocompromised Patients: Diagnosis by Blood Culture and Fecal Examination, Antimicrobial Susceptibility Tests, and Morphological and Seroagglutination Characteristics," *Journal of Clinical Microbiology*, vol. 21, No. 2, Feb. 1985, pp. 168–173.

Macher, Abe M. M.D. et al., "Bacteremia Due to Mycobacterium avium–intracellulare in the Acquired Immunodeficiency Syndrome," *Annals of Internal Medicine*, 1983:99:782–785.

Ellis, John, "Cellular biochemistry, Proteins as Molecular Chapaerones," *Nature*, vol. 328, 30 Jul. 1987, pp. 378–379.

Clark–Curtiss, Josephine E., et al., "Molecular Analysis of DNA and Construction of Genomic Libraries of *Mycobacterium leprae*," *Journal of Bacteriology*, Mar. 1985, vol. 161, No. 3, pp. 1093–1102.

Young, Richard A., et al., "Dissection of *Mycobacterium tuberculosis* antigens using recombinant DNA," *Proc. Natl. Acad. Sci. USA*, vol. 82, pp. 2583–2587, May 1985.

Young, Richard A., et al., "Genes for the Major Protein Antigens of the Leprosy parasite *Mycobacterium leprae*, "*Nature*, vol. 316, 1 Aug. 1985, pp. 450–452.

Lu, Melvin C., et al., "Genes for Immunodominant Protein Antigens Are Highly Homologous in *Mycobacterium tuberculosis*, *Mycobacterium Africanum*, and the Vaccine Strain *Mycobacterium Bovis* BCG," *Infection and Immunity*, Oct. 1987, vol. 55, No. 10, pp. 2378–2382.

Husson, Robert N., et al., "Genes for the Major Protein Antigens of *Mycobacterium Tuberculosis*: The etiologic agents of tuberculosis and leprosy share an immunodominant antigen," *Proc. Natl. Acad. Sci. USA*, vol. 84, pp. 1679–1683, Mar. 1987.

Andersen, Ase Bengard, et al., "Isolation and Characterization of Recombinant Lambda gt11 Bacteriophages Expressing Eight Different Mycobacterial Antigens of Potential Immunological Relevance," *Infection and Immunity*, May 1988, vol. 56, No. 5, pp. 1344–1351.

Shinnick, Thomas M., "The 65–Kilodalton Antigen of *Mycobacterium tuberculosis*," *Journal of Bacteriology*, Mar. 1987, vol. 169, No. 3, pp. 1080–1088.

Thole, Jelle E., et al., "Cloning of *Mycobacterium bovis* BCG DNA and Expression of Antigens in *Escherichia coli*," *Infection and Immunity*, Dec. 1985, vol. 50, No. 3, pp. 800–806.

Mehra, Vijay, et al., "Efficient Mapping of Protein Antigenic Determinants," *Proc. Natl. Acad. Sci. USA*, vol. 83, pp. 7013–7017, Sep. 1986.

Hance, A. J., et al., "Detection and Identification of Mycobacteria by Amplification of Mycobacterial DNA," *Molecular Microbiology*, (1989) 3(7), pp. 843–849.

Thole, Jelle E. R., et al., "Characterization, Sequence Determination, and Immunogenicity of a 64–Kilodalton Protein of *Mycobacterium bovis* BCG Expressed in *Escherichia coli* K–12," *Infection and Immunity*, vol. 55, No. 6, Jun. 1987, pp. 1466–1475.

Sjobring, Ulf., et al., "Polymerase Chain Reaction for Detection of *Mycobacterium Tuberculosis*," *Journal of Clinical Microbiology*, vol. 28, No. 1, Oct. 1990, pp. 2200–2204.

Saiki, Randall K., et al., "Primer–Directed Enzymatic Amplification of DNA with a Thermostable DNA Polymerase," *Science*, vol. 239, pp. 487–491.

Stead, et al., "Changing Faces of Clinical Tuberculosis," *Mycobacterium tuberculosis*, Interacting with the Immune System, Plenum, NY 1988, pp. 371–388.

1988 Stratagere Catalog, p. 39.

Primary Examiner—Stephanie W. Zitomer
Assistant Examiner—Scott W. Houtteman
Attorney, Agent, or Firm—Oliff & Berridge

[57] ABSTRACT

Nucleotide fragment of DNA, whose nucleotide sequence is included in the gene of the species of the genus Mycobacterium, coding for the 65-kD mycobacterial antigen, containing regions which are homologous in practically all species of the genus Mycobacterium, and at least one species-specific variable region, characterized in that said fragment is chosen from fragments whose nucleotide sequences possess at least 70% homology, and preferably at least 85% homology, with a predetermined sequence or its complementary sequence, said predetermined sequence beginning at nucleotide 438 and ending at nucleotide 751 of said gene coding for said antigen of all species of mycobacteria except for the species *M. tuberculosis, M. bovis BCG, M. avium, M. paratuberculosis, M. fortuitum, M. malmoense, M. leprae, M. kansaii* and *M. marinum*.

9 Claims, 3 Drawing Sheets

FIG.1A

```
         578                                          598                                          618                                          638
    (1)  CGGCCAACCCG CTCGGTCTCA AACGCGGCAT CGAAAAGGCC GTGGAGAAGG TCACCGAGAC CCTGCTCAAG
    (2)  ----------- ---------- ---------- ---------- ---------- ---------- -----------
    (3)  ----------- ---------- ---------- ---------- ---------- ---------- -----------
    (4)  ----------- ---------- ---------- ---------- ---------- ---------- -----------
    (5)  ----------- ---------- ---------- ---------- ---------- ---------- -----------
    (6)  ----------- ----C--G-- ---------- ---------- ----C--CC- ----T-G--A -----------
    (7)  ----------- --G----G-- ---------- -G-------- ----C--C-- ---------- -----------
    (8)  ------A---- --G------- ---------- -G-------- ----C----- ---------- -----------
    (9)  ----------- --G------- ---------- -G-------- ----C----- ---------- -----------
   (10)  ----------- --G------- ---------- -G-------- ----C----- ---------- -----------
   (11)  ----------- ----C--G-- ---------- -G-------- ----C----- ---------- -G------G--
   (12)  T---------- ----A-C--- ---------- -G------G- ---C------ ---------- -----------
   (13)  ----------- ---GA-C--- ---------- -G------G- ---C------ ---------- -----------
   (14)  ----------- ------A--- --C--T---- -G-----CTG --C--T---- -A--T----T -----------

648                                          668                                          688                                          708
    (1)  GGCGCCAAGG AGGTGAGAGAC CAAGGAGCAG ATTGCGGCCA CCGCAGCGAT TTCGGCGGGT GACCAGTCCA
    (2)  ---------- ----------- ---------- ---------- ---------- ---------- -----------
    (3)  ---------- ----------- ---------- ---------- ---------- ---------- -----------
    (4)  ---------- ----------- ---------- ---------- ---------- ---------- -----------
    (5)  ---------- ----------- ---------- ---------- ---------- ---------- -----------
    (6)  TCG------- ----------- -------C-- ----C--C-- ----C-G--- ---C--C--- ---A-CA----
    (7)  TCG----A-- ----------- -------C-- ----C--T-- ----G--C-- ---C--C--- ---------G-
    (8)  TCG------- ----------- -------C-- ----C--T-- ----G--C-- -G-C--C--- ---------CGG-
    (9)  TCG------- ----------- -------C-- ----C--T-- ----G--C-- ---C--C--- ---------G-
   (10)  TCG------- ----------- -------C-- ----C--T-- ----G--C-- ---C--C-C- ---------G-
   (11)  A--------- -----G----- ---------- ----C--T-- ----C-GT-- -C-C--C--- -----------
   (12)  TCG------- ----------- -------C-- ----C--T-G -----C---- ---C------ ---------G-
   (13)  TCG------- ----------- -----A-C-- ----C--C-- ----G----- -G-C------ ---------G-
   (14)  -A-------- ----------- --A-A----- ----T----- ----T----- -T-------- ---------G-
```

(1) TUBERCULOSIS
(2) BOVIS BCG
(3) BOVIS
(4) MICROTI
(5) AFRICANUM
(6) CHITAE
(7) INTRACEL. 3324
(8) INTRACELLULARE
(9) AVIUM
(10) PARATUBERCULOSIS
(11) FORTUITUM
(12) MALMOENSE
(13) SCROFULACEUM
(14) LEPRAE

FIG. 1B

| | | 718 | | 738 | | 758 | | 778 | |
|---|---|---|---|---|---|---|---|---|---|
| TUBERCULOSIS | (1) | TCGGTGACCT | GATCGCCGAG | GCGATGGACA | AGGTGGGCAA | CGAGGGCGTC | ATCACCGTCG | AGGAGTCCAA | (SEQ ID NO: 22) |
| BOVIS BCG | (2) | ---------- | - | | | | | | |
| BOVIS | (3) | ---------- | - | | | | | | |
| MICROTI | (4) | ---------- | - | | | | | | |
| AFRICANUM | (5) | ---------- | - | | | | | | |
| CHITAE | (6) | ---------- | - | | | | | | |
| INTRACEL. 3324 | (7) | ----C----- | - | | | | | | |
| INTRACELLULARE | (8) | | | | | | | | |
| AVIUM | (9) | ----C----- | - | | | | | | |
| PARATUBERCULOSIS | (10) | ----C----- | - | | | | | | |
| FORTUITUM | (11) | ---------- | ---------- | --C------- | ---- | | | | |
| MALMOENSE | (12) | ----C----- | - | | | | | | |
| SCROFULACEUM | (13) | ----C----- | - | | | | | | |
| LEPRAE | (14) | ------T--- | ---------- | ---------- | ---- | | | | |

FIG. 1C

DNA FRAGMENTS, PROBES AND AMPLIFICATION PRIMERS OF THE 65 KD ANTIGEN OF MYCOBACTERIA

The genus Mycobacterium includes at least 54 species (Wayne, L. G., and Kubica, G. P. 1986. Genus Mycobacterium. In "Bergey's Manual of Systematic Bacteriology" (P. H. A. Sneath, N. Mair, and M. E. Sharp, eds.). Vol. 2, pp. 1436–1457. Williams & Wilkins, Baltimore, Md.). Most of these species are saprophytes and do not cause human or veterinary diseases. The mycobacteria pathogenic to man which are the most important in terms of morbidity and mortality are *Mycobacterium tuberculosis* and *M. leprae,* which cause tuberculosis and leprosy. Tuberculosis remains one of the major infectious diseases of the planet, with around 10 million new cases and 3 million deaths per annum (Stylbo, K. 1983, Tuberculosis and its control: Lessons to be learned from past experience and its implications for leprosy control programmes. Ethiop. Med. J. 21:101–122 and World Health Organisation. 1986. Results of a World Health Organisation-sponsored workshop to characterize antigens recognized by Mycobacterium-specific monoclonal antibodies. Infect. Immun. 51:718–720).

In Europe, Africa and North America, a recent trend towards an increase in prevalence seems to be discernible, no doubt linked to the multiplication of cases of AIDS (Stead, W. W., and Dutt, A. K. 1988. Changing faces of clinical tuberculosis. In *Mycobacterium tuberculosis.* Interactions with the Immune System" (M. Bendinelli and H. Friedman, eds.) pp. 371–388. Plenum, N.Y.)

*M. tuberculosis* is taxonomically very close to *M. bovis, M. africanum* (which also cause tuberculosis in man) and *M. microti* (tuberculosis of certain rodents), so that these four species are collectively named the "*M. tuberculosis* complex" (Wayne L. G. et al.). Among non-tuberculous mycobacteria (sometimes called "atypical"), there should be mentioned the increased incidence of mycobacteria belonging to the *M. avium-intracellulare* complex in immunosuppressed patients (AIDS, transplantations, cancer treatments, etc.) (Kielin, T. E., Edwards, F. F., Brannon, P., Tsang, A. Y., Maio, M., Gold, J. W. M., Whimby, E., Wong, B., McClatchy, J. K., and Amstrong, D. 1985. Infections caused by *Mycobacterium avium* complex in immunocompromised patients: Diagnosis by blood culture and fecal examination, antimicrobial susceptibility tests and morphological and seroagglutination characteristics. J. Clin. Microbiol. 21, 168–173. Macher, A. M., M. Kovacs, J. A. Gill, V., Roberts, G. D., Ames, J., Parke, C. H., Strans, S., Lane, H. C., Parillo, J. E., Fanci, A. S., and Masur, H. 1983. Bacteremia due to *Mycobacterium avium-intracellulare* in the acquired immunodeficiency syndrome. Ann. Intern. Med. 99, 782–785).

This complex comprises the species *M. avium, M. intracellulare* (very closely related to one another, whence the term *M. avium-intracellulare*), *M. paratuberculosis* (the cause of Johne's disease in calves) and *M. lepraemurium* (rat leprosy). Other species produce human infections of lesser importance in terms of seriousness or morbidity, such as *M. kansasii* (adentitis), *M. ulcerans* and *M. marinum* (skin ulcerations).

Virtually all the mycobacteria possess a characteristic and specific antigen, termed 65-kD antigen, which has been completely sequenced and identified.

The 65-kD antigen possesses numerous characteristics of interest which have led to extensive studies. In the first place, this protein appears to be a major mycobacterial antigen. The individuals or animals infected or immunized with mycobacteria produce antibodies and T cells which recognize this antigen in the large majority of cases, and this has made it possible, moreover, to dissect the epitopes from it. Next, the 65-kD antigen belongs to the family of "heat shock" proteins or thermal shock proteins, which are also to be found with a high degree of conservation in many prokaryotic and eukaryotic cells. These proteins function as a "chaperon" in the post-translational assembling of certain proteins of prokaryotes, chloroplasts and mitochondria (Ellis J. 1988. Nature 328: 378–9). Lastly, special interest also attaches to the 65-kD antigen inasmuch as it has been associated with the pathogenesis of autoimmune arthritis (Thole, J. E. R., and Van Der Zee, R. 1990. The 65-kD antigen: molecular studies on a ubiquitous antigen. In: Molecular Biology of the Mycobacteria, J. Mc Fadden Ed., Surrey University Press, London, pp. 37–67).

These numerous points of interest explain why this antigen has been one of the very first to be cloned and sequenced in various mycobacteria (Clark-Curtiss, J. E., Jacobs, W. R., Docherty, M. A., Richtie, L. R., and Curtiss III, R. 1985. J. Bacteriol. 161, 1093–102. Young R. A., Blooms, B. R., Grosskinsky, C. M., Ivangi, J., Thomas, D. and Davis R. W. 1985. Proc. Natl. Acad. Sci. USA. 42:2583–7 Young, R. A., Mehra, V., Sweeetser, D., Buchanan, T., Clark-Curtiss, J., Dasvis, R. W., and Bloom, B. R. 1985. Genes for the major protein antigens of the leprosy parasite *Mycobacterium leprae.* Nature. 316:450–2. Lu, M. C., Lien, M. H., Becken, R. E., Heine, H. C., Buggo, A. M., Lipovsek, D., et al. 1987. Infect. Imm. 55:23–82. Husson R. N., and Young R. A., 1987. Proc. Natl. Acad. Sci. USA. 84:1679–83. Andersen, A. S., Worsaae, A. and Chaparas, S. D. 1988. Infect. Imm. 56:1344–51. Shinnick, T. M. 1987. The 65-kilodalton antigen of *Mycobacterium tuberculosis.* J. Bacteriol. 169:1080–88. Thols, J. E. R., Dauwesse, H. G., Das, P. K., Croothuis, D. G., Shouls, L. M. and Embden, J. D. A. 1985. Cloning of *Mycobacterium bovis* BCG DNA and expression of antigens in *Escherichia coli.* Inf. Imm. 50:800–6. Mehra, V., Sweetser D., and Young, R. A. 1986. Efficient mapping of protein antigenic determinants. Proc. Natl. Acad. Sci. USA. 83:7013–17.).

The document WO-A-8800974, referred to in the reference of Young R. A. et al., Nature, 1985, 376:450–2 describes a DNA sequence coding for the 65-kD antigen of *M. leprae,* the document WO-A-8806591 describes a DNA sequence coding for the 65-kD antigen of *M. tuberculosis* referred to in the Shinnick et al. reference, and the publication of Thole et al, Infect. Immunol., 1987, 55:1466–71 describes a DNA sequence coding for the 65-kD antigen of *M. bovis* BCG.

However, all the techniques of qualitative and/or quantitative characterization or identification of mycobacteria described in the prior art, directly from their nucleic acids, still possess the following drawbacks.

The genomic DNA sequence selected for the purpose of identifying virtually constant regions (falling within the notion of homology) in the genus Mycobacterium, and/or variable regions which are, respectively, specific to the species belonging to said genus, is not conserved in most mycobacteria known at present. It is, in general, conserved only for a few species, thereby rendering the process of identification non-selective for the whole of the genus Mycobacterium.

More recently, the document WO-A-9012875 described a 383-base pair nucleotide sequence of the gene coding for the 65-kD antigen in *M. tuberculosis, M. bovis* BCG, *M. avium, M. paratuberculosis, M. fortuitum, M. malmoense, M. leprae, M. kansaii* and *M. marinum,* on the basis of which sequence probes for the identification of some of the above-mentioned species or groups of species were determined; as well as primers for the amplification of DNA fragments belonging to said gene.

Nevertheless, regions selected in the prior art are conserved only for a few species, so that the primer or primers determined for amplifying these regions do not hybridize with the genomic DNA of some species, as demonstrated by the results obtained with the primers TB1 and TB2 according to WO-A-90 12875 and shown in Table 2.

The objective of the present invention is to remedy the above drawbacks. More specifically, the subject of the invention is:

1) a sequence of the genomic DNA of mycobacteria, belonging to the gene coding for the KD 65 mycobacterial antigen, comprising regions which are virtually constant for the majority of species of mycobacteria;

2) any specific primer for amplification, by DNA polymerization, of the sequence according to (1) which is virtually constant for the majority of species belonging to the *M tuberculosis* and/or *M avium-intracellulare* complex;

3) one or more detection probes, termed genus probes, which hybridize with a portion of the sequence according to (1) which is virtually constant for the majority of species belonging to the genus Mycobacterium;

4) one or more detection probes, termed species probes, which hybridize with a portion of the sequence according to (1) which is virtually constant for the majority of species belonging to the *M tuberculosis* and/or *M avium-intracellulare* complex;

5) any reagent or reagents involving one or more isolated sequences according to (1), and/or primers according to (2), and/or genus probes according to (3), and/or species probes according to (4).

BRIEF DESCRIPTION OF THE DRAWINGS

FIG. 1A–C shows a sequence comparison of a portion of the 64-kD antigen for several Mycobacteria species.

The terms probes and/or primers as used in the present invention refer to a natural DNA or RNA fragment, or a natural or synthetic oligonucleotide, or a synthetic DNA or RNA fragment which is unmodified or comprises one or more modified bases such as inosine, 5-methyldeoxycytidine, deoxyuridine, 5-dimethlaminodeoxyuridine, 2,6-diaminopurine, 5-bromodeoxyuridine or any other modified base permitting hybridization, it being possible for the DNA fragment to be single- or double-stranded.

According to the present invention, there is provided, in the first place, a single-stranded DNA fragment, isolated or forming part of a double-stranded DNA macromolecule, whose nucleotide sequence is included in the gene of the species of the genus Mycobacterium, coding for the so-called 65-kD mycobacterial antigen, containing regions which are constant or homologous in practically all species of the genus Mycobacterium, and one or more variable regions which are specific, that is to say constant or homologous for a given species. According to the invention, and on the basis of the sequencing of the abovementioned gene established by Shinnick (Schinnick TM 1987, J. Bacteriol. 169: 1080–88), said fragment is chosen from fragments whose nucleotide sequences possess at least 70% homology, and preferably at least 85% homology, with a predetermined or reference sequence, or homologous with the sequence complementary to this chosen predetermined or reference sequence according to the invention, said predetermined sequence beginning at nucleotide 438 and ending at nucleotide 751 of said gene coding for said 65-kD antigen of all species of mycobacteria except for the species *M. tuberculosis, M. bovis BCG, M. avium, M. paratuberculosis, M. fortuitum, M. malmoense, M. leprae, M. kansaii* and *M. marinum*.

Before describing the invention, various terms used in the description and claims are now defined:

according to the invention, a nucleotide fragment is a string of monomers capable of hybridizing with a nucleotide fragment under predetermined conditions, it being possible for the string to contain monomers of different structures and to be obtained from a natural nucleic acid molecule and/or by genetic recombination and/or by chemical synthesis, thus, a monomer can be a natural nucleotide of nucleic acid whose constituent elements are a sugar, a phosphate group and a nitrogenous base; in DNA, the sugar is ribose, in RNA, the sugar is 2-deoxyribose; depending on whether the nucleic acid is DNA or RNA, the nitrogenous base is chosen from adenine, guanine, uracil, cytosine and thymine; or a nucleotide which is modified in at least one of the three constituent elements; as an example, the modification can take place in the bases, generating modified bases such as incsine, 5-methyldeoxycytidine, deoxyuridine, 5-dimethylaminodeoxyuridine, 2,6-diaminopurine, 5-bromodeoxyuridine and any other modified base promoting hybridization, in the sugar, namely the replacement of at least one deoxyribose by a polyamide (P. E. Nielsen et al., Science, 254, 1497–1500 (1991)), or in the phosphate group, for example its replacement by esters chosen, in particular, from diphosphate, alkyl- and arylphosphonate and phosphorothioate esters, complementary sequence is understood to mean any sequence which hybridizes completely with the predetermined or reference sequence, hybridization is understood to mean the process during which, under suitable conditions, two nucleotide fragments having sufficiently complementary sequences pair to form a double strand, a probe is a nucleotide fragment comprising from 5 to 100 monomers, and advantageously from 10 to 40 monomers, possessing a specificity of hybridization under particular conditions to form a hybridization complex with a nucleotide fragment having a nucleotide sequence included in the genomic DNA of mycobacteria; a probe may be used for diagnostic purposes, for instance capture and/or detection probes, the capture probe may be immobilized on a solid support by any suitable means, that is to say directly or indirectly, for example by covalent bonding or passive adsorption, the detection probe is labeled by means of a label chosen from radioactive isotopes, enzymes chosen, in particular, from peroxidase and alkaline phosphatase and those capable of hydrolyzing a chromogenic, fluorogenic or luminescent substrate, chromophoric chemical compounds, chromogenic, fluorogenic or luminescent compounds, nucleotide base analogs and biotin, the probes used for diagnostic purposes of the invention may be employed in all known hybridization techniques, and in particular the techniques termed "DOT-BLOT" (MANIATIS et al, Molecular Cloning, Cold Spring Harbor, 1982), "SOUTHERN BLOT" (SOUTHERN. E. M., J. Mol. Biol., 98, 503 (1975), "NORTHEN BLOT", a technique identical to the "SOUTHERN BLOT" technique but which uses RNA as target, and the SANDWICH technique (DUNN A. R., HASSEL J. A., Cell, 12, 23 (1977)); advantageously, the SANDWICH technique is used in the present invention, comprising a specific capture probe and/or a specific detection probe, it being understood that the capture probe and the detection probe must possess an at least partially different nucleotide sequence, a primer is a probe comprising from 5 to 30 monomers, and preferably 15 to 25 monomers, possessing a specificity of hybridization under particular conditions for the initiation of an enzymatic polymerization, for example in an amplification technique such as PCR (Polymerase Chain Reaction), in an elongation method such as sequencing, in a transcription method or the like, homology characterizes the degree of similarity of two nucleotide fragments which are compared.

As an example of fragments according to the invention, the sequence of the single-stranded fragment possesses at least 70% homology, and preferably at least 85% homology, with any one of the sequences SEQ ID N01, SEQ ID N02, SEQ ID N03, SEQ ID N04, SEQ ID N05 and SEQ ID N07 identified at the end of the description.

By means of the single-stranded fragment according to the invention, amplified with all suitable primers and detected with all genus and species probes determined below, all the mycobacteria tested, namely 21 strains representing 19 species, responded positively to the test performed, under circumstances where comparable tests, for example according to the document WO-A-90 12875, enable only 15 strains out of 21 to be amplified, consequently leaving 6 strains of mycobacteria undetected.

The invention also relates to any macromolecule of genomic or isolated DNA, or of RNA, comprising or integrating a single-stranded fragment as defined above. There corresponds to this definition, in particular, any replication vector incorporating a said fragment, but also any amplification product resulting from the labeling with suitable primers of a nucleotide sequence corresponding to the predetermined sequence defined above, to within at least 70% homology; in this case, a nucleotide sequence the central portion of which corresponds, in single-stranded form, to the predetermined sequence, flanked by the two amplification primers, for example, is obtained.

On the basis of the predetermined sequence selected, the invention has defined various specific primers for the amplification by polymerization of the genomic DNA of a bacterium of the genus Mycobacterium. Generally speaking, such a primer comprises a nucleotide sequence enabling it to hybridize a so-called constant region of this predetermined sequence which is homologous or identical for practically all species of the genus Mycobacterium, in particular the region beginning at nucleotide 438 and ending at nucleotide 457, and the region beginning at nucleotide 733 and ending at nucleotide 751, again according to Shinnick's sequencing.

This primer advantageously comprises between 15 and 25 monomers.

As an example, this primer possesses a nucleotide sequence chosen from SEQ ID N08 and SEQ ID N09, identified at the end of the description.

Any amplification technique may be used and, in particular, all pairs of primers as defined above, for example all pairs of primers comprising at least 10 bases of the sequences SEQ ID N08 and SEQ ID N09, will be selected.

Still on the basis of the same single-stranded fragment according to the invention, the latter also provides a so-called genus probe, capable of hybridizing a constant region of said fragment which is homologous or constant for practically all species of the genus Mycobacterium.

Preferably, this genus probe is capable of hybridizing an end region of the single-stranded fragment according to the invention, corresponding to a primer as defined above, integrated in or linked to said fragment.

However, this genus probe can hybridize any other constant region of the same single-stranded fragment; advantageously, these probes possess a nucleotide sequence chosen from SEQ ID N010 and SEQ ID N011, identified at the end of the description.

Still on the basis of the same single-stranded fragment according to the invention, other subjects of the latter are various species probes, each comprising a nucleotide sequence enabling it to hybridize a so-called variable region of said predetermined sequence, identified above, this variable region being specific to at least one species of the genus Mycobacterium.

According to an important feature, the present invention provides in addition probes specific for groups of species corresponding to the *M. tuberculosis* and *M. avium-intracellulare* complexes, respectively. These probes comprise a nucleotide sequence enabling them to hybridize a variable region of the fragment whose sequence is included in the gene coding for 65-kD, said region being common to several species of the same complex.

Preferably, these species or complex probes comprise from 10 to 40 monomers.

Advantageously, the nucleotide sequence of the probe is chosen from SEQ ID N012 and SEQ ID N013 to SEQ ID N021, identified at the end of the description.

According to the invention, a reagent or reagent kit is provided for selectively detecting a bacterium of the genus Mycobacterium, belonging to the *M. tuberculosis* and *M. avium-intracellulare* complexes, in a biological sample. Such a kit comprises, where appropriate one or more primers as described above, where appropriate one or more genus probes as described above, and one or more species probes as described above.

Depending on the hybridization technique used, the probe or probes according to the invention are in a liquid medium and/or bound directly or indirectly to a solid support. As regards the solid support according to the invention, in all suitable form such as tube, cone, well, microtitration plate, sheet or soluble polymer, this is chosen from polystyrenes, styrene/butadiene copolymers and styrene/butadiene copolymers mixed with polystyrenes, polypropylenes, polycarbonates, polystyrene/acrylonitrile copolymers, styrene/methyl methylmethacrylate [sic] copolymers, from synthetic and natural fibers and from polysaccharides and cellulose derivatives.

The invention also relates to a method for selectively detecting a bacterium of the genus Mycobacterium in a biological sample. This method entails the following steps:

preparation of samples in order to release the mycobacterial nucleic acid hybridization of the genomic DNA and/or RNA of the bacterium, and/or of its transcribed RNA, with at least one primer as defined above; multiplication of the DNA or RNA fragment flanked by said primer or primers, to obtain a multitude of single-stranded DNA and/or RNA fragments corresponding to the definition according to the invention; these two steps are optional, their object being to avoid culture of the bacteria exposure of the fragment or fragments to at least one species probe and/or at least one genus probe as defined above.

The present invention is now described according to Examples 1 to 5, and in support of Tables 1 and 2 and of FIG.

Figure 1A:
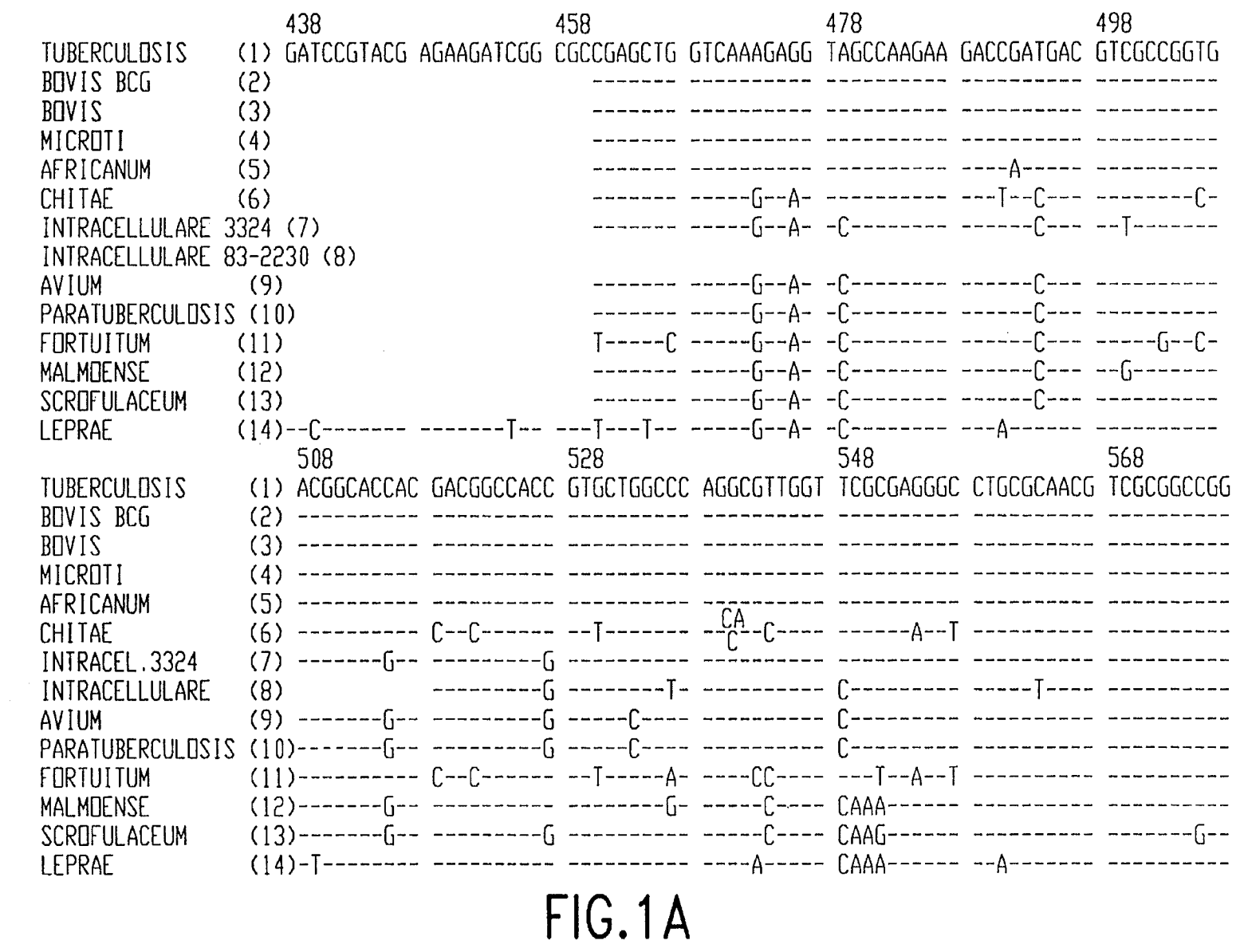

1, which is divided into FIG. 1a, 1b and 1c and which shows the alignment of the nucleotide sequences (according to the numbering of Shinnick et al. 1987) over a 314-bp portion of the gene coding for the 65-kD antigen of mycobacteria; the sequences of the strains of the following species are taken from the literature:

M. tuberculosis (Document WO-A-8806591 and Shinnick, T. M. 1987. The 65-kilodalton antigen of *Mycobacterium tuberculosis*. J. Bacteriol. 169:1080–88)

M. bovis BCG (Thole et al. 1987. Characterization, sequence determination, and immunogenicity of a 64-kilodalton protein of *Mycobacterium bovis BCG* expressed in *Escherichia coli* K-12. Inf. Imm. 55:1466–1475).

M. avium, M. fortuitum and M. paratuberculosis (Document FR-A-2,645,878 and Hance, A. J., Grandchamp, B., Lévy-Frébault, V., Lecossier, D., Rauzier, J., Bocart, D., and Gicquel, B. 1989. Detection and identification of mycobacterium by amplification of mycobacterial DNA. Molecul. Microbiol. 3:843–9.)

Mycobacterium leprae (Young, R. A., Mehra, V., Sweeetser, D., Buchanan, T, Clark-Curtiss, J., Davis, R. W., and Bloom, B. R. 1985. Genes for the major protein antigens of the leprosy parasite *Mycobacterium leprae*. Nature. 316:450–2)

The sequences of the following species were determined using strains available to the Applicant: M. africanum, M. microti, M. chitae, M. intracellulare 3324, M. intracellulare 83 2230, M. malmoense, M. scrofulaceum.

According to FIGS. 1a to 1c, a dash means that the base is identical to that identified on the first line.

Table 1 shows oligonucleotide sequences according to the invention, exemplified below, and their specificity.

TABLE 1

Synthetic oligonucleotides used as polymerization primers or probe for detecting a portion of the gene for the 65-kD antigen of mycobacteria, and whose specificity is at the level of genus or of species of mycobacteria (*) the figures in brackets indicate the position of the oligonucleotide according to the numbering of Shinnick et al., 1987; C. indicates a homology with the complementary strand.

| Oligonucleotide | Sequence* |
|---|---|
| Polymerization or amplification primers | |
| SEQ ID NO8: GAT CCG TAC GAG AAG ATC GG | (438–457) |
| SEQ ID NO9: ACC TTG TCC ATC GCC TCG G | (C.733–751) |
| Genus hybridization probes: | |
| SEQ ID NO11: CGC AAC GTC GCG GCC GGC GCC AAC CCG C | (561–588) |
| SEQ ID NO10: CCG AGG CGA TGG ACA AGG T | (733–751) |
| **Hybridization probes for the *avium-intracellulare* complex:** | |
| SEQ ID NO21: TGC TCA AGT CGG CCA AGG | (640–657) |
| SEQ ID NO13: ACG GCA CGA CGA CGG | (508–522) |
| SEQ ID NO14: CCA CGG TGC TSG CYC AGG | (523–540) |
| SEQ ID NO15: GAC CAG YSG ATC GGC GAC C | (708–726) |
| SEQ ID NO16: CCG CTG GGT CTS AA | (585–598) |
| SEQ ID NO17: GCG TTG GTC CGC GAG GGC C | (540–558) |
| SEQ ID NO18: CGA CGA CGG CCA CGG TGC T | (514–532) |
| SEQ ID NO19: CCG CTG GGT CTS AAG CGC G | (585–603) |
| SEQ ID NO20: CCA AMC CGC TGG GTC TSA A | (580–598) |
| Hybridization probe for the tuberculosis complex: | |
| SEQ ID NO12: GGT CAA AGA GGT AGC CAA G | (467–485) |

Table 2 shows the specificities of enzymatic amplification and of hybridization of the bacterial strains tested. In this table:

as regards the source, the FIGS. 1 refer to strains available from the Centre de Collection des Mycobactéries, [Collection Center for Mycobacteria], CHUV at Lausanne, 2 to the Centre Médical Universitaire [University Medical Center] in Geneva, 3 to the Institut d'Hygiène [Hygiene Institute] in Geneva and Bio M to the laboratories of bioMérieux TB1 and TB2 refere to primers according to the document WO-A-90 12875.

TABLE 2

| | | | | HYBRIDIZATION OF THE AMPLIFICATION PRODUCT, and labeling of the radioactive $^{32}$P probe ($^{32}$P) or enzymatic detection (cold) | | |
|---|---|---|---|---|---|---|
| | | AMPLIFICATION | | GENUS | GENUS | M. tuberculosis |
| SPECIES | SOURCE | TB1–TB2 | SEQ ID NO8 SEQ ID NO9 | SEQ ID NO 11 ($^{32}$P) | SEQ ID NO 10 (cold) | Complex SEQ ID N012 (cold) |
| M. tuberculosis | 2 | + | + | + | + | + |
| M. microti | 3 | + | + | + | + | + |

TABLE 2-continued

| | | AMPLIFICATION | | HYBRIDIZATION OF THE AMPLIFICATION PRODUCT, and labeling of the radioactive $^{32}$P probe ($^{32}$P) or enzymatic detection (cold) | | |
|---|---|---|---|---|---|---|
| | | | | GENUS | GENUS | M. tuberculosis |
| SPECIES | SOURCE | TB1–TB2 | SEQ ID NO8 SEQ ID NO9 | SEQ ID NO 11 ($^{32}$P) | SEQ ID NO 10 (cold) | Complex SEQ ID N012 (cold) |
| M. bovis | 3 | + | + | + | + | + |
| M. africanum La 1077 | 1 | NP | + | + | + | + |
| M. kansasii | 3 | + | + | + | + | NP |
| M. marinum 2417 | 3 | + | + | + | + | NP |
| M. simiae ATCC 25275 | BIoM | NP | + | + | + | . |
| M. scrofulaceum | 3 | + | + | + | + | NP |
| M. gordonae | BIoM | + | + | + | + | . |
| M. szulgai | 3 | + | + | + | + | NP |
| M. flavescens | BIoM | NP | + | + | + | . |
| M. intracellulare 83-2230 | 2 | . | + | + | + | NP |
| M intracellulare 83-3324 | 2 | . | + | + | + | . |
| M. intracellulare ATCC 357 64 | BoIM | NF | + | + | + | . |
| M. avium | 2 | + | + | + | + | NP |
| M. avium-intracellulare 4556 | 3 | + | + | + | + | . |
| M. xenopi 4333 | 3 | NF | + | + | + | NP |
| M. terrae ATCC 15755 | BIoM | + | + | + | + | NP |
| M. malmoense | 3 | NP | + | + | + | NP |
| M. nonchlomogenicum | 3 | NP | + | + | + | . |
| M. triviale ATCC 23 292 | BIoM | NP | + | + | + | NP |
| M. gastri | 1 | NP | + | NP | + | . |
| M. farcinogenos | 3 | NP | + | NP | + | NP |
| M. haomophilum | 1 | NP | + | NP | + | . |
| M. ulcerans | 1 | NP | + | NE | + | . |
| M. paratuberculosis | 1 | NP | + | + | + | . |
| M. chelonei | 2 | . | + | + | + | . |
| M. chelonei ATCC 14472 | BIoM | NP | + | + | + | NP |
| M. fortuitum 83-3359 | 2 | + | + | + | + | . |
| M. diernhoferi | 3 | + | + | + | + | NP |
| M. chitae | 3 | + | + | + | + | NP |
| M. chelonei-abscessus | 3 | NP | + | + | + | NP |
| M. senegalese | 3 | NP | + | + | + | NP |
| M. vaccae | 3 | . | + | + | + | NP |
| M. phlei | 3 | + | + | + | + | . |
| M. thermoresistibile | 3 | . | + | + | + | NP |
| M. smegmatis | 3 | . | + | + | + | NP |
| Nocardia asteroides 864 | 2 | NP | . | . | . | NP |
| Nocardia asteroides 866 | 2 | NP | . | . | . | NP |
| Nocardia asteroides 869 | 2 | NP | . | . | . | NP |
| Nocardia asteroides 870 | 2 | NP | . | . | . | NP |
| Nocardia caviae 861 | 2 | NP | . | . | . | NP |

1 centre de collection des mycobactéries [Collection center for mycobacteria], Lausanne, 2 Centre Médical Universitaire [University Medical Center] in Geneva, 3 Institut d'hygiene [Hygiène Institute] In Geneva
NP: not performed

EXAMPLE NO. 1

Definition of genus-specific amplification primers and their use

After various preliminary experiments, it was found that the sequences provided in the literature as "universal" primers for the genus Mycobacterium do not respond to some strains or species known at present; thus, the primers termed TB1 and TB2 according to the document WO-A-90 12875 do not respond to some species, as indicated above.

A sequencing of the gene coding for the 65-kD antigen was hence carried out in various species in which said gene had not yet been explored. By alignment of the sequences thereby obtained with those already described in the prior art, new primers which were discovered to hybridize with the sequences conserved in practically all mycobacteria were then chosen; see SEQ ID N08 and SEQ ID N09 in Table 1. This discovery was made by amplification from a strain of mycobacteria. The technique used is described below.

Extraction of genomic DNA was performed according to the protocol of Sjöbring (SjöSbring et al. 1990. Polymerase chain reaction for detection of Mycobacterium tuberculosis. J.Clin. Microbiol. 28(10):2200–2204). 200 ml of liquid culture are centrifuged at 2600 rpm for 15 min. The supernatant is discarded and the pellets are pooled. The pellet is washed with pH 8.0 buffer (50 mM Tris base, 50 mM NaCl, 5 mMEDTA, pH 8.0). 0.1 volume of 10×digestion buffer (100 mM Tris pH 8.0, 200 mM EDTA, 10% SDS) and proteinase K at a concentration of 5 mg/ml final are added. The mixture is incubated at 60° C. for 3 hours with stirring and heated for 5 minutes to 100° C. to inactivate the proteinase K. The DNA is precipitated a first time by adding a solution of 0.4 volume of cetyltrimethylammonium bromide solution (5% in 0.4M NaCl) and the mixture is incubated for 15 minutes at temperature [sic] and then 15 min at 4° C. It is transferred to Eppendorf tubes and centrifuged for 15 min at 12,000 rpm. The supernatant is discarded and the pellet is washed in TE (Tris EDTA) buffer (10 mM Tris pH 7.5, 1 mM EDTA). The DNA is precipitated a second time after extraction with phenol/chloroform (1:1)/ isoamyl alcohol (24:1). The DNA is precipitated with 2 volumes of absolute ethanol and 0.1 volume of 3M sodium acetate.

The DNA is amplified according to the PCR technique of Saiki et al. (Saiki et al. 1988. Primer-directed enzymatic amplification of DNA with a thermostable DNA polymerase) using a Dri-Bock PCH-1 PCR apparatus (TECHNE, Great Britain). The reaction medium consists of Tris.Cl 10 mmol/l; $MgCl_2$ 1.5 mmol/l; KCl 50 mmol/l; gelatin 1 mg/ml; dATP, dCTP, dGTP, dTTP 0.5 mmol/l each; pH 8.3; oligonucleotide TB1 (according to the document WO-A-90 12875, 25 pmol; oligonucleotide TB2 (according to the document WO-A-90 12875), 25 pmol; and 10 µl of the bacterial DNA preparation. After denaturation for 5 min followed by centrifugation, the enzyme is added at a concentration of 1.5 U/reaction. PCR is performed over 27 cycles with the parameters 96° C./43° C./74° C., for 1 min, 1 min and 0.7 min, respectively.

The amplified DNA is analyzed by electrophoresis on 0.8% agarose gel in TBE (Tris Borate EDTA) buffer (89 mM Tris base, 89 mMboric acid, 2 mMEDTA). The bands are visualized with ethidium bromide.

EXAMPLE NO. 2

Determination of nucleotide sequences of various species of mycobacteria and sequence alignment.

Starting with the total DNA isolated as above, a portion of the gene coding for the 65-kD antigen was amplified using the primers SEQ ID N08 and SEQ ID N09 in Table 1. The amplification products obtained were sequenced directly using the Gibco BRL kit (thermal cycling). The various sequences obtained are presented in FIG. 1.

EXAMPLE NO. 3

Determination of genus- and species-specific oligonucleotide probes and their use on DNA samples amplified according to Example No. 1.

The PCR amplification products obtained using the primers SEQ ID N08 and SEQ ID N09 (Table 2) were tested with various species or genus probes described in Table 1, according to the Dot-Blot technique.

The substrate DNA of the amplification reaction is extracted by a technique different from that of Example 1: after centrifugation of an aliquot of $10^7$ mycobacteria in 0.5% Tween, the bacteria are suspended in a Tris-HCl buffer (pH 8.0, 50 mM), and are then subjected to sonication for 10 min at 55° C. in the presence of siliconed 10 µm glass beads, and then to boiling for 5 min. 10 µl of the lysate are then amplified according to the PCR protocol described in Example No. 1.

Hybridization of the species or genus oligonucleotides was performed according to the protocol described by Ausubel FM, Brent R, Kingston RE, Moore DD, Smith JA, Seidman JG and Struhl K (1987) Current protocols in molecular biology, Green publishing Associated and Wiley intersciences, New York. The oligonucleotides are labeled by kinasing with [gamma(or [lacuna])-$^{32}$P]-ATP (5000 Ci/mol), and the temperatures and washing conditions are as follows, for example for MYC3: 59° C. 30 min in 1×SSC (Saline Sodium Citrate: 0.15M NaCl, 0.015M $Na_3$ citrate (2 $H_2O$ pH 7.0), 1% SDS.

EXAMPLE NO. 4

Species typing of mycobacteria by hybridization of a mycobacterial genus amplification product using oligonucleotide probes, carried out using a non-radioactive and semi-automated detection system described in the document FR-A-2,663,040.

The amplification products obtained in Example No. 3 were tested again according to the cold probe technology described below according to two variants.

The first technique employs a microtitration plate format.

A solution of the capture oligonucleotide at a concentration of 1 ng/µl in 3×PBS (0.45M NaCl, 0.15M sodium phosphate, pH 7.0) is placed in a microtitration plate (Nunc 439454). The capture probe or oligonucleotide is chosen from the oligonucleotides described in Table 2 (SEQ ID N011, SEQ ID N010, SEQ ID N012, SEQ ID N021 and SEQ ID N013 to SEQ ID N020) which are specific for the genus or for various species of mycobacteria. Their position in the sequence is indicated in FIG. 1. The plate is incubated for 2 h at 37° C. and then washed 3 times with 300 µl of PBST (1×PBS, 0.5% Tween 20 (Merck 822184)). The target consisting of 4 µl of the amplified product is mixed with 76 µl of salmon PBS buffer (3×PBS +10 µg/ml salmon sperm DNA (Sigma D9156) and 10 µl of 2N sodium hydroxide. The mixture is neutralized 5 min later by adding 10 µl of 2N acetic acid. The mixture is added into the well in addition to 50 µl of a solution of the oligonucleotide-peroxidase conjugate at a concentration of 0.5 ng/µl of oligonucleotide in a horse PBS buffer (3×PBS+10% horse serum (BioMérieux 55842). The oligonucleotide-peroxidase conjugate constitutes the detection probe and possesses the nucleotide sequence of SEQ ID N010. The plate is incubated for 1 h at 37° C. and washed with 3×300 µl of PBST. Into each well, 100 µl of OPD substrate (ortho-phenylenediamine, Cambridge Medical Biotechnology ref/456) are added in a suitable buffer (0.055M citric acid, 0.1M $Na_2HPO_4$, pH 4.93) at a concentration of 4 mg/ml, to which 30-volumes $H_2O_2$ diluted to 1/1000 is added immediately before use. After 20 min of reaction, the enzymatic activity is blocked with 100 µl of 1N $H_2SO_4$ and reading is performed on an Axia Microreader apparatus (Axia, BioMérieux registered trademark) at 492 nm.

The specificity results are given in Table 2. They indicate that the probe MYC 2-S [sic] is specific for the genus Mycobacterium, and that the probe TUB 1-S [sic] is specific only for the species of the *tuberculosis* complex. Moreover, the probe may be labeled using a radiactive isotope, a suitable enzyme, a fluorochrome, a base analog or a compound involved in a luminescence reaction. In addition, the probe can have a diphosphate, alkyl- or acrylphosphorate or phosphorothioate ester skeleton or a skeleton of the polyamide type.

The second technique employs the format of the VIDAS automated apparatus (bioMérieux, France, registered trademark).

We claim:

1. A nucleotide fragment consisting of nucleotides 438 to 751 of a gene coding for a 65-kD mycobacterial antigen or a fully complementary sequence.

2. The fragment of claim 1, wherein said fragment consists of SEQ ID NO: 23 or its fully complementary sequence.

3. A nucleotide fragment consisting of a nucleotide sequence that is at least 85% homologous with a predetermined sequence or its complementary sequence, said predetermined sequence consisting of nucleotides 438 to 751 of a gene coding for a 65-kD mycobacterial antigen, wherein said fragment comprises a nucleotide sequence selected from the group of sequences consisting of SEQ ID NO: 1, SEQ ID: NO: 2, SEQ ID NO: 3, SEQ ID NO: 4, SEQ ID NO: 5, SEQ ID NO: 6; SEQ ID NO: 7; and their respective fully complementary sequences and said fragment contains at least one region which is homologous in practically all species of Mycobacterium and at least on species-specific variable region.

4. A specific primer for the amplification of a genomic DNA of Mycobacterium, wherein said primer is capable of specifically hybridizing to constant region of a single stranded fragment defined in claim 1 and comprises a nucleotide sequence selected from the group consisting of SEQ ID NO: 8; SEQ ID NO: 9; and their respective fully complementary sequences.

5. A probe specific for *M. tuberculosis* complex and capable of specifically hybridizing a region of a single-stranded fragment defined in claim 1 of a gene of a species of said complex that codes for a 65-kD antigen, said probe comprising a nucleotide sequence having at least 85% homology with the sequence of SEQ ID NO: 12 or a fully complementary sequence of SEQ ID NO: 12.

6. The probe of claim 5, said probe comprising a nucleotide sequence of SEQ ID NO: 12 or a fully complementary sequence of SEQ ID NO: 12.

7. A probe specific for *M. avium-intracellulare* complex and capable of specifically hybridizing a region of a single-stranded fragment defined in claim 1 of a gene of a species of said complex that codes for a 65-kD antigen, said probe comprising a nucleotide sequence having at least 85% homology with a sequence selected from the group of sequences consisting of SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20; SEQ ID NO: 21; and their respective fully complementary sequences.

8. The probe of claim 7, said probe comprising a nucleotide sequence selected from the group of sequences consisting of SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20; SEQ ID NO: 21; and their respective fully complementary sequences.

9. A probe consisting of a nucleotide sequence selected from the group consisting of SEQ ID NO: 10; SEQ ID NO: 11; and their respective fully complementary sequences.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 268 base pairs
        ( B ) TYPE: nucleic acid
        ( C ) STRANDEDNESS: single-stranded
        ( D ) TOPOLOGY: linear ( i i ) MOLECULE TYPE: DNA (genomic)

( i i i ) HYPOTHETICAL:

( i v ) ANTI-SENSE:

( v i ) ORIGINAL SOURCE:
        ( A ) ORGANISM: Mycobacterium bovis
        ( B ) STRAIN:
&nbs

```
CGAGCTGGTC  AAAGAGGTAG  CCAAGAAGAC  CGATGACGTC  GCCGGTGACG  GCACCACGAC      60

GGCCACCGTG  CTGGCCCAGG  CGTTGGTTCG  CGAGGGCCTG  CGCAACGTCG  CGGCCGGCGC     120

CAACCCGCTC  GGTCTCAAAC  GCGGCATCGA  AAAGGCCGTG  GAGAAGGTCA  CCGAGACCCT     180

GCTCAAGGGC  GCCAAGGAGG  TCGAGACCAA  GGAGCAGATT  GCGGCCACCG  CAGCGATTTC     240

GGCGGGTGAC  CAGTCCATCG  GTGACCTG                                           268
```

( 2 ) INFORMATION FOR SEQ ID NO:3:

( i ) SEQUENCE CHARACTERISTICS:
        ( A ) LENGTH: 268 base pairs
        ( B ) TYPE: nucleic acid
        ( C ) STRANDEDNESS: single- stranded
        ( D ) TOPOLOGY: linear ( i i ) MOLECULE TYPE: DNA (genomic)

( i i i ) HYPOTHETICAL:

( i v ) ANTI-SENSE:

( v i ) ORIGINAL SOURCE:
        ( A ) ORGANISM: Mycobacterium africanum
        ( B ) STRAIN:
        ( C ) INDIVIDUAL ISOLATE:

( v i i i ) POSITION IN GENOME:
        ( A ) CHROMOSOME/SEGMENT:
        ( B ) MAP POSITION:

( i x ) FEATURE:
        ( A ) NAME/KEY:
        ( B ) LOCATION: 461-728
        ( C ) IDENTIFICATION METHOD:
        ( D ) OTHER INFORMATION:

( x i ) SEQUENCE DESCRIPTION: SEQ ID NO:3:

```
CGAGCTGGTC  AAAGAGGTAG  CCAAGAAGAC  CAATGACGTC  GCCGGTGACG  GCACCACGAC      60

GGCCACCGTG  CTGGCCCAGG  CGTTGGTTCG  CGAGGGCCTG  CGCAACGTCG  CGGCCGGCGC     120

CAACCCGCTC  GGTCTCAAAC  GCGGCATCGA  AAAGGCCGTG  GAGAAGGTCA  CCGAGACCCT     180

GCTCAAGGGC  GCCAAGGAGG  TCGAGACCAA  GGAGCAGATT  GCGGCCACCG  CAGCGATTTC     240

GGCGGGTGAC  CAGTCCATCG  GTGACCTG                                           268
```

( 2 ) INFORMATION FOR SEQ ID NO:4:

( i ) SEQUENCE CHARACTERISTICS:
        ( A ) LENGTH: 268 base pairs
        ( B ) TYPE: nucleic acid
        ( C ) STRANDEDNESS: single- stranded
        ( D ) TOPOLOGY: linear ( i i ) MOLECULE TYPE: DNA (genomic)

( i i i ) HYPOTHETICAL:

( i v ) ANTI-SENSE:

( v i ) ORIGINAL SOURCE:
        ( A ) ORGANISM: Mycobacterium chitae
        ( B ) STRAIN:
        ( C ) INDIVIDUAL ISOLATE:

( v i i i ) POSITION IN GENOME:
        ( A ) CHROMOSOME/SEGMENT:
        ( B ) MAP POSITION:

( i x ) FEATURE:
        ( A ) NAME/KEY:
        ( B ) LOCATION: 461-728

(C) IDENTIFICATION METHOD:
(D) OTHER INFORMATION:

(xi) SEQUENCE DESCRIPTION: SEQ ID NO:4:

| | | | | | | |
|---|---|---|---|---|---|---|
| CGAGCTGGTC | AAGGAAGTAG | CCAAGAAGAC | TGACGACGTC | GCCGGCGACG | GCACCACCAC | 60 |
| CGCCACCGTT | CTGGCCCASV | CGCTGGTTCG | CGAAGGTCTG | CGCAACGTCG | CGGCCGGCGC | 120 |
| CAACCCGCTC | GGCCTGAAGC | GCGGCATCGA | GAAGGCCGTC | GAGACCGTCT | CGGAGAACCT | 180 |
| GCTCAAGTCG | GCCAAGGAGG | TCGAGACCAA | GGAGCAGATC | GCCGCCACCG | CCGGGATCTC | 240 |
| CGCGGGCGAC | AACACCATCG | GTGACCTG | | | | 268 |

(2) INFORMATION FOR SEQ ID NO:5:

(i) SEQUENCE CHARACTERISTICS:
        (A) LENGTH: 268 bases
        (B) TYPE: nucleic acid
        (C) STRANDEDNESS: single-stranded
        (D) TOPOLOGY: linear (ii) MOLECULE TYPE: DNA (genomic)

(iii) HYPOTHETICAL:

(iv) ANTI-SENSE:

(vi) ORIGINAL SOURCE:
        (A) ORGANISM: Mycobacterium intracellulare
        (B) STRAIN:
        (C) INDIVIDUAL ISOLATE:

(viii) POSITION IN GENOME:
        (A) CHROMOSOME/SEGMENT:
        (B) MAP POSITION:

(ix) FEATURE:
        (A) NAME/KEY:
        (B) LOCATION: 461-728
        (C) IDENTIFICATION METHOD:
        (D) OTHER INFORMATION:

(xi) SEQUENCE DESCRIPTION: SEQ ID NO:5:

| | | | | | | |
|---|---|---|---|---|---|---|
| CGAGCTGGTC | AAGGAAGTCG | CCAAGAAGAC | CGACGACGTT | GCCGGTGACG | GCACGACGAC | 60 |
| GGCCACGGTG | CTGGCCCAGG | CGTTGGTTCG | CGAGGGCCTG | CGCAACGTCG | CGGCCGGCGC | 120 |
| CAACCCGCTG | GGTCTGAAGC | GCGGCATCGA | GAAGGCCGTC | GACAAGGTCA | CCGAGACCCT | 180 |
| GCTCAAGTCG | GCCAAAGAGG | TCGAGACCAA | GGACCAGATC | GCTGCCACCG | CGGCCATTTC | 240 |
| GGCGGGCGAC | CAGTCGATCG | GCGACCTG | | | | 268 |

(2) INFORMATION FOR SEQ ID NO:6:

(i) SEQUENCE CHARACTERISTICS:
        (A) LENGTH: 200 base pairs
        (B) TYPE: nucleic acid
        (C) STRANDEDNESS: single-stranded
        (D) TOPOLOGY: linear (ii) MOLECULE TYPE: DNA (genomic)

(iii) HYPOTHETICAL:

(iv) ANTI-SENSE:

(vi) ORIGINAL SOURCE:
        (A) ORGANISM: Mycobacterium intralcellulare
        (B) STRAIN:
        (C) INDIVIDUAL ISOLATE:

(viii) POSITION IN GENOME:
        (A) CHROMOSOME/SEGMENT:
        (B) MAP POSITION:

( i x ) FEATURE:
    ( A ) NAME/KEY:
    ( B ) LOCATION: 518-717
    ( C ) IDENTIFICATION METHOD:
    ( D ) OTHER INFORMATION:

( x i ) SEQUENCE DESCRIPTION: SEQ ID NO:6:

| | | | | | | |
|---|---|---|---|---|---|---|
| GACGGCCACG | GTGCTGGCTC | AGGCGTTGGT | CCGCGAGGGC | CTGCGTAACG | TCGCGGCCGG | 60 |
| CGCCAAACCG | CTGGGTCTCA | AGCGCGGCAT | CGAGAAGGCC | GTCGAGAAGG | TCACCGAGAC | 120 |
| CCTGCTCAAG | TCGGCCAAGG | AGGTCGAGAC | CAAGGACCAG | ATCGCTGCCA | CCGCGGCCAT | 180 |
| TTCGGCGGGC | GACCAGCGGA | | | | | 200 |

( 2 ) INFORMATION FOR SEQ ID NO:7:

( i ) SEQUENCE CHARACTERISTICS:
    ( A ) LENGTH: 268 base pairs
    ( B ) TYPE: nucleic acid
    ( C ) STRANDEDNESS: single-stranded
    ( D ) TOPOLOGY: linear ( i i ) MOLECULE TYPE: DNA (genomic)

( i i i ) HYPOTHETICAL:

( i v ) ANTI-SENSE:

( v i ) ORIGINAL SOURCE:
    ( A ) ORGANISM:
    ( B ) STRAIN:
    ( C ) INDIVIDUAL ISOLATE:

( v i i i ) POSITION IN GENOME:
    ( A ) CHROMOSOME/SEGMENT:
    ( B ) MAP POSITION:

( i x ) FEATURE:
    ( A ) NAME/KEY:
    ( B ) LOCATION: 461-728
    ( C ) IDENTIFICATION METHOD:
    ( D ) OTHER INFORMATION:

( x i ) SEQUENCE DESCRIPTION: SEQ ID NO:7:

| | | | | | | |
|---|---|---|---|---|---|---|
| CGAGCTGGTC | AAGGAAGTCG | CCAAGAAGAC | CGACGACGTC | GCCGGTGACG | GCACGACGAC | 60 |
| GGCCACGGTG | CTGGCCCAGG | CGCTGGTCAA | GGAGGGCCTG | CGCAACGTCG | CGGCGGGCGC | 120 |
| CAACCCGCTG | AGCCTCAAGC | GCGGCATCGA | GAAGGCGGTC | GAGAAGGTCA | CCGAGACCCT | 180 |
| GCTCAAGTCG | GCCAAGGAGG | TCGAGACCAA | GGACCAGATC | GCCGCCACCG | CGGCGATTTC | 240 |
| GGCGGGCGAC | CAGTCGATCG | GCGACCTG | | | | 268 |

( 2 ) INFORMATION FOR SEQ ID NO:8:

( i ) SEQUENCE CHARACTERISTICS:
    ( A ) LENGTH: 20 base pairs
    ( B ) TYPE: nucleic acid
    ( C ) STRANDEDNESS: single-stranded
    ( D ) TOPOLOGY: linear ( i i ) MOLECULE TYPE: DNA (genomic)

( i i i ) HYPOTHETICAL:

( i v ) ANTI-SENSE:

( v i ) ORIGINAL SOURCE:
    ( A ) ORGANISM:
    ( B ) STRAIN:
    ( C ) INDIVIDUAL ISOLATE:

( v i i i ) POSITION IN GENOME:

(A) CHROMOSOME/SEGMENT:
(B) MAP POSITION:

(ix) FEATURE:
(A) NAME/KEY:
(B) LOCATION: 438-457
(C) IDENTIFICATION METHOD:
(D) OTHER INFORMATION:

(xi) SEQUENCE DESCRIPTION: SEQ ID NO:8:

GATCCGTACG AGAAGATCGG                    20

(2) INFORMATION FOR SEQ ID NO:9:

(i) SEQUENCE CHARACTERISTICS:
(A) LENGTH: 19 base pairs
(B) TYPE: nucleic acid
(C) STRANDEDNESS: single-stranded
(D) TOPOLOGY: linear (ii) MOLECULE TYPE: DNA (genomic)

(iii) HYPOTHETICAL:

(iv) ANTI-SENSE:

(vi) ORIGINAL SOURCE:
(A) ORGANISM:
(B) STRAIN:
(C) INDIVIDUAL ISOLATE:

(viii) POSITION IN GENOME:
(A) CHROMOSOME/SEGMENT:
(B) MAP POSITION:

(ix) FEATURE:
(A) NAME/KEY:
(B) LOCATION: 733-751
(C) IDENTIFICATION METHOD:
(D) OTHER INFORMATION:

(xi) SEQUENCE DESCRIPTION: SEQ ID NO:9:

ACCTTGTCCA TCGCCTCGG                     19

(2) INFORMATION FOR SEQ ID NO:10:

(i) SEQUENCE CHARACTERISTICS:
(A) LENGTH: 19 base pairs
(B) TYPE: nucleic acid
(C) STRANDEDNESS: single-stranded
(D) TOPOLOGY: linear (ii) MOLECULE TYPE: DNA (genomic)

(iii) HYPOTHETICAL:

(iv) ANTI-SENSE:

(vi) ORIGINAL SOURCE:
(A) ORGANISM:
(B) STRAIN:
(C) INDIVIDUAL ISOLATE:

(viii) POSITION IN GENOME:
(A) CHROMOSOME/SEGMENT:
(B) MAP POSITION:

(ix) FEATURE:
(A) NAME/KEY:
(B) LOCATION: 733-751
(C) IDENTIFICATION METHOD:
(D) OTHER INFORMATION:

(xi) SEQUENCE DESCRIPTION: SEQ ID NO:10:

CCGAGGCGAT GGACAAGGT                     19

( 2 ) INFORMATION FOR SEQ ID NO:11:

( i ) SEQUENCE CHARACTERISTICS:
        ( A ) LENGTH: 28 base pairs
        ( B ) TYPE: nucleic acid
        ( C ) STRANDEDNESS: single- stranded
        ( D ) TOPOLOGY: linear ( i i ) MOLECULE TYPE: DNA (genomic)

( i i i ) HYPOTHETICAL:

( i v ) ANTI-SENSE:

( v i ) ORIGINAL SOURCE:
        ( A ) ORGANISM:
        ( B ) STRAIN:
        ( C ) INDIVIDUAL ISOLATE:

( v i i i ) POSITION IN GENOME:
        ( A ) CHROMOSOME/SEGMENT:
        ( B ) MAP POSITION:

( i x ) FEATURE:
        ( A ) NAME/KEY:
        ( B ) LOCATION: 561-588
        ( C ) IDENTIFICATION METHOD:
        ( D ) OTHER INFORMATION:

( x i ) SEQUENCE DESCRIPTION: SEQ ID NO:11:

CGCAACGTCG CGGCCGGCGC CAACCCGC     28

( 2 ) INFORMATION FOR SEQ ID NO:12:

( i ) SEQUENCE CHARACTERISTICS:
        ( A ) LENGTH: 19 base pairs
        ( B ) TYPE: nucleic acid
        ( C ) STRANDEDNESS: single- stranded
        ( D ) TOPOLOGY: linear ( i i ) MOLECULE TYPE: DNA (genomic)

( i i i ) HYPOTHETICAL:

( i v ) ANTI-SENSE:

( v i ) ORIGINAL SOURCE:
        ( A ) ORGANISM:
        ( B ) STRAIN:
        ( C ) INDIVIDUAL ISOLATE:

( v i i i ) POSITION IN GENOME:
        ( A ) CHROMOSOME/SEGMENT:
        ( B ) MAP POSITION:

( i x ) FEATURE:
        ( A ) NAME/KEY:
        ( B ) LOCATION: 467-485
        ( C ) IDENTIFICATION METHOD:
        ( D ) OTHER INFORMATION:

( x i ) SEQUENCE DESCRIPTION: SEQ ID NO:12:

GGTCAAAGAG GTAGCCAAG     19

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: single- stranded
        ( D ) TOPOLOGY: linear ( i i ) MOLECULE TYPE: DNA (genomic)

( i i i ) HYPOTHETICAL:

( i v ) ANTI-SENSE:

( v i ) ORIGINAL SOURCE:
    ( A ) ORGANISM:
    ( B ) STRAIN:
    ( C ) INDIVIDUAL ISOLATE:

( v i i i ) POSITION IN GENOME:
    ( A ) CHROMOSOME/SEGMENT:
    ( B ) MAP POSITION:

( i x ) FEATURE:
    ( A ) NAME/KEY:
    ( B ) LOCATION: 508-522
    ( C ) IDENTIFICATION METHOD:
    ( D ) OTHER INFORMATION:

( x i ) SEQUENCE DESCRIPTION: SEQ ID NO:13:

ACGGCACGAC GACGG     15

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single- stranded
        ( D ) TOPOLOGY: linear ( i i ) MOLECULE TYPE: DNA (genomic)

( i i i ) HYPOTHETICAL:

( i v ) ANTI-SENSE:

( v i ) ORIGINAL SOURCE:
        ( A ) ORGANISM:
        ( B ) STRAIN:
        ( C ) INDIVIDUAL ISOLATE:

( v i i i ) POSITION IN GENOME:
        ( A ) CHROMOSOME/SEGMENT:
        ( B ) MAP POSITION:

( i x ) FEATURE:
        ( A ) NAME/KEY:
        ( B ) LOCATION: 523-540
        ( C ) IDENTIFICATION METHOD:
        ( D ) OTHER INFORMATION:

( x i ) SEQUENCE DESCRIPTION: SEQ ID NO:14:

CCACGGTGCT SGCYCAGG     18

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single- stranded
        ( D ) TOPOLOGY: linear ( i i ) MOLECULE TYPE: DNA (genomic)

( i i i ) HYPOTHETICAL:

( i v ) ANTI-SENSE:

( v i ) ORIGINAL SOURCE:
        ( A ) ORGANISM:
        ( B ) STRAIN:
        ( C ) INDIVIDUAL ISOLATE:

( v i i i ) POSITION IN GENOME:
        ( A ) CHROMOSOME/SEGMENT:
        ( B ) MAP POSITION:

( i x ) FEATURE:
            ( A ) NAME/KEY:
            ( B ) LOCATION: 708-726
            ( C ) IDENTIFICATION METHOD:
            ( D ) OTHER INFORMATION:

( x i ) SEQUENCE DESCRIPTION: SEQ ID NO:15:

GACCAGYSGA TCGGCGACC                                                                                          19

( 2 ) INFORMATION FOR SEQ ID NO:16:

( i ) SEQUENCE CHARACTERISTICS:
            ( A ) LENGTH: 14 base pairs
            ( B ) TYPE: nucleic acid
            ( C ) STRANDEDNESS: single- stranded
            ( D ) TOPOLOGY: linear ( i i ) MOLECULE TYPE: DNA (genomic)

( i i i ) HYPOTHETICAL:

( i v ) ANTI-SENSE:

( v i ) ORIGINAL SOURCE:
            ( A ) ORGANISM:
            ( B ) STRAIN:
            ( C ) INDIVIDUAL ISOLATE:

( v i i i ) POSITION IN GENOME:
            ( A ) CHROMOSOME/SEGMENT:
            ( B ) MAP POSITION:

( i x ) FEATURE:
            ( A ) NAME/KEY:
            ( B ) LOCATION: 585-598
            ( C ) IDENTIFICATION METHOD:
            ( D ) OTHER INFORMATION:

( x i ) SEQUENCE DESCRIPTION: SEQ ID NO:16:

CCGCTGGGTC TSAA                                                                                               14

( 2 ) INFORMATION FOR SEQ ID NO:17:

( i ) SEQUENCE CHARACTERISTICS:
            ( A ) LENGTH: 19 base pairs
            ( B ) TYPE: nucleic acid
            ( C ) STRANDEDNESS: single- stranded
            ( D ) TOPOLOGY: linear ( i i ) MOLECULE TYPE: DNA (genomic)

( i i i ) HYPOTHETICAL:

( i v ) ANTI-SENSE:

( v i ) ORIGINAL SOURCE:
            ( A ) ORGANISM:
            ( B ) STRAIN:
            ( C ) INDIVIDUAL ISOLATE:

( v i i i ) POSITION IN GENOME:
            ( A ) CHROMOSOME/SEGMENT:
            ( B ) MAP POSITION:

( i x ) FEATURE:
            ( A ) NAME/KEY:
            ( B ) LOCATION: 540-558
            ( C ) IDENTIFICATION METHOD:
            ( D ) OTHER INFORMATION:

( x i ) SEQUENCE DESCRIPTION: SEQ ID NO:17:

GCGTTGGTCC GCGAGGGCC                                                                                          19

( 2 ) INFORMATION FOR SEQ ID NO:18:

( i ) SEQUENCE CHARACTERISTICS:
        ( A ) LENGTH: 19 base pairs
        ( B ) TYPE: nucleic acid
        ( C ) STRANDEDNESS: single- stranded
        ( D ) TOPOLOGY: linear ( i i ) MOLECULE TYPE: DNA (genomic)

( i i i ) HYPOTHETICAL:

( i v ) ANTI-SENSE:

( v i ) ORIGINAL SOURCE:
        ( A ) ORGANISM:
        ( B ) STRAIN:
        ( C ) INDIVIDUAL ISOLATE:

( v i i i ) POSITION IN GENOME:
        ( A ) CHROMOSOME/SEGMENT:
        ( B ) MAP POSITION:

( i x ) FEATURE:
        ( A ) NAME/KEY:
        ( B ) LOCATION: 514-532
        ( C ) IDENTIFICATION METHOD:
        ( D ) OTHER INFORMATION:

( x i ) SEQUENCE DESCRIPTION: SEQ ID NO:18:

CGACGACGGC CACGGTGCT                                                                    19

( 2 ) INFORMATION FOR SEQ ID NO:19:

( i ) SEQUENCE CHARACTERISTICS:
        ( A ) LENGTH: 19 base pairs
        ( B ) TYPE: nucleic acid
        ( C ) STRANDEDNESS: single- stranded
        ( D ) TOPOLOGY: linear ( i i ) MOLECULE TYPE: DNA (genomic)

( i i i ) HYPOTHETICAL:

( i v ) ANTI-SENSE:

( v i ) ORIGINAL SOURCE:
        ( A ) ORGANISM:
        ( B ) STRAIN:
        ( C ) INDIVIDUAL ISOLATE:

( v i i i ) POSITION IN GENOME:
        ( A ) CHROMOSOME/SEGMENT:
        ( B ) MAP POSITION:

( i x ) FEATURE:
        ( A ) NAME/KEY:
        ( B ) LOCATION: 585-603
        ( C ) IDENTIFICATION METHOD:
        ( D ) OTHER INFORMATION:

( x i ) SEQUENCE DESCRIPTION: SEQ ID NO:19:

CCGCTGGGTC TSAAGCGCG                                                                    19

( 2 ) INFORMATION FOR SEQ ID NO:20:

( i ) SEQUENCE CHARACTERISTICS:
        ( A ) LENGTH: 19 base pairs
        ( B ) TYPE: nucleic acid
        ( C ) STRANDEDNESS: single- stranded
        ( D ) TOPOLOGY: linear ( i i ) MOLECULE TYPE: DNA (genomic)

( i i i ) HYPOTHETICAL:

( i v ) ANTI-SENSE:

( v i ) ORIGINAL SOURCE:
    ( A ) ORGANISM:
    ( B ) STRAIN:
    ( C ) INDIVIDUAL ISOLATE:

( v i i i ) POSITION IN GENOME:
    ( A ) CHROMOSOME/SEGMENT:
    ( B ) MAP POSITION:

( i x ) FEATURE:
    ( A ) NAME/KEY:
    ( B ) LOCATION: 580-598
    ( C ) IDENTIFICATION METHOD:
    ( D ) OTHER INFORMATION:

( x i ) SEQUENCE DESCRIPTION: SEQ ID NO:20:

CCAAMCCGCT GGGTCTSAA          19

( 2 ) INFORMATION FOR SEQ ID NO:21:

( i ) SEQUENCE CHARACTERISTICS:
    ( A ) LENGTH: 18 base pairs
    ( B ) TYPE: nucleic acid
    ( C ) STRANDEDNESS: single- stranded
    ( D ) TOPOLOGY: linear ( i i ) MOLECULE TYPE: DNA (genomic)

( i i i ) HYPOTHETICAL:

( i v ) ANTI-SENSE:

( v i ) ORIGINAL SOURCE:
    ( A ) ORGANISM:
    ( B ) STRAIN:
    ( C ) INDIVIDUAL ISOLATE:

( v i i i ) POSITION IN GENOME:
    ( A ) CHROMOSOME/SEGMENT:
    ( B ) MAP POSITION:

( i x ) FEATURE:
    ( A ) NAME/KEY:
    ( B ) LOCATION: 640-657
    ( C ) IDENTIFICATION METHOD:
    ( D ) OTHER INFORMATION:

( x i ) SEQUENCE DESCRIPTION: SEQ ID NO:21:

TGCTCAAGTC GGCCAAGG          18

( 2 ) INFORMATION FOR SEQ ID NO:22:

( i ) SEQUENCE CHARACTERISTICS:
    ( A ) LENGTH: 350 base pairs
    ( B ) TYPE: nucleic acid
    ( C ) STRANDEDNESS: single- stranded
    ( D ) TOPOLOGY: linear ( i i ) MOLECULE TYPE: DNA (genomic)

( i i i ) HYPOTHETICAL:

( i v ) ANTI-SENSE:

( v i ) ORIGINAL SOURCE:
    ( A ) ORGANISM: Mycobacterium tuberculosis
    ( B ) STRAIN:
    ( C ) INDIVIDUAL ISOLATE:

( v i i i ) POSITION IN GENOME:
    ( A ) CHROMOSOME/SEGMENT:
    ( B ) MAP POSITION:

( i x ) FEATURE:

(A) NAME/KEY:
        (B) LOCATION: 438-787
        (C) IDENTIFICATION METHOD:
        (D) OTHER INFORMATION:

(xi) SEQUENCE DESCRIPTION: SEQ ID NO:22:

GATCCGTACG AGAAGATCGG CGCCGAGCTG GTCAAAGAGG TAGCCAAGAA GACCGATGAC    60

GTCGCCGGTG ACGGCACCAC GACGGCCACC GTGCTGGCCC AGGCGTTGGT TCGCGAGGGC    120

CTGCGCAACG TCGCGGCCGG CGCCAACCCG CTCGGTCTCA AACGCGGCAT CGAAAAGGCC    180

GTGGAGAAGG TCACCGAGAC CCTGCTCAAG GGCGCCAAGG AGGTCGAGAC CAAGGAGCAG    240

ATTGCGGCCA CCGCAGCGAT TTCGGCGGGT GACCAGTCCA TCGGTGACCT GATCGCCGAG    300

GCGATGGACA AGGTGGGCAA CGAGGCGTC ATCACCGTCG AGGAGTCCAA                350

(2) INFORMATION FOR SEQ ID NO:23:

(i) SEQUENCE CHARACTERISTICS:
        (A) LENGTH: 314 base pairs
        (B) TYPE: nucleic acid
        (C) STRANDEDNESS: single-stranded
        (D) TOPOLOGY: linear (ii) MOLECULE TYPE: DNA (genomic)

(iii) HYPOTHETICAL:

(iv) ANTI-SENSE:

(vi) ORIGINAL SOURCE:
        (A) ORGANISM: Mycobacterium tuberculosis
        (B) STRAIN:
        (C) INDIVIDUAL ISOLATE:

(viii) POSITION IN GENOME:
        (A) CHROMOSOME/SEGMENT:
        (B) MAP POSITION:

(ix) FEATURE:
        (A) NAME/KEY:
        (B) LOCATION: 438-751
        (C) IDENTIFICATION METHOD:
        (D) OTHER INFORMATION:

(xi) SEQUENCE DESCRIPTION: SEQ ID NO:23:

GATCCGTACG AGAAGATCGG CGCCGAGCTG GTCAAAGAGG TAGCCAAGAA GACCGATGAC    60

GTCGCCGGTG ACGGCACCAC GACGGCCACC GTGCTGGCCC AGGCGTTGGT TCGCGAGGGC    120

CTGCGCAACG TCGCGGCCGG CGCCAACCCG CTCGGTCTCA AACGCGGCAT CGAAAAGGCC    180

GTGGAGAAGG TCACCGAGAC CCTGCTCAAG GGCGCCAAGG AGGTCGAGAC CAAGGAGCAG    240

ATTGCGGCCA CCGCAGCGAT TTCGGCGGGT GACCAGTCCA TCGGTGACCT GATCGCCGAG    300

GCGATGGACA AGGT                                                      314